United States Patent [19]
Bragg et al.

[11] Patent Number: 5,403,266
[45] Date of Patent: Apr. 4, 1995

[54] INFLATABLE CERVICAL TRACTION COLLAR

[75] Inventors: Steven Bragg, Jamul; Frederick J. Koolhof, El Cajon; Vick G. Bonessa, Arcadia, all of Calif.

[73] Assignee: United States Manufacturing Company, Pasadena, Calif.

[21] Appl. No.: 88,563

[22] Filed: Jul. 6, 1993

[51] Int. Cl.6 .................................................. A61F 5/00
[52] U.S. Cl. ............................................. 602/5; 602/13; 602/18
[58] Field of Search ................. 602/5, 12, 13, 17, 18; 128/DIG. 20, DIG. 23; 5/630, 636, 637

[56] References Cited

U.S. PATENT DOCUMENTS

| | | | |
|---|---|---|---|
| 2,389,690 | 11/1945 | Schreiber | 602/18 |
| 3,042,027 | 7/1962 | Monfardini | 128/75 |
| 3,135,256 | 6/1964 | Gruber | 128/75 |
| 3,164,151 | 1/1965 | Nicoll | 602/18 |
| 3,343,532 | 9/1967 | Zumaglini | 602/18 |
| 3,397,688 | 8/1968 | Gottfried | 602/13 |
| 3,610,235 | 10/1971 | Vagacs | 602/13 |
| 3,916,885 | 11/1975 | Gaylord, Jr. | 128/75 |
| 4,099,523 | 7/1978 | Lowrey | 128/75 |
| 4,520,801 | 6/1985 | Lerman | 128/75 |
| 4,682,588 | 7/1987 | Curlee | 602/13 |
| 5,060,637 | 10/1991 | Schmid | 602/18 |
| 5,060,661 | 10/1991 | Howard | 602/13 |

OTHER PUBLICATIONS

Glacier Cross, Inc. TM PRONEX TM A patient-controlled pneumatic device for the comfortable and secure management of cervical pain, Glacier Cross, Inc. Healthcare Products, Aug. 1992, 3 pages.

Primary Examiner—Michael A. Brown
Attorney, Agent, or Firm—Christie, Parker & Hale

[57] ABSTRACT

A cervical traction collar capable of ambulatory use by a patient comprises a pair of elongated overlying semi-rigid flexible upper and lower support members secured at their ends to encircle the neck, with releasable attachment means such as Velcro fasteners securing the overlying upper and lower support members for adjusting the height of the collar. A tubular, flexible, air-inflatable bladder is secured to the collar so as to project downwardly away from a bottom edge of the lower support member continuously around the bottom of the collar. The bladder is filled with air under pressure from a manually operated air pump to inflate the bladder so that it presses downwardly against the shoulder region of the patient continuously around the lower neck region. This expands the height of the collar to apply an upward force around the base of the chin and the left and right mandibular and occipital region of the patient to maintain a controlled uniform amount of traction force encircling the cervical region of the patient.

7 Claims, 6 Drawing Sheets

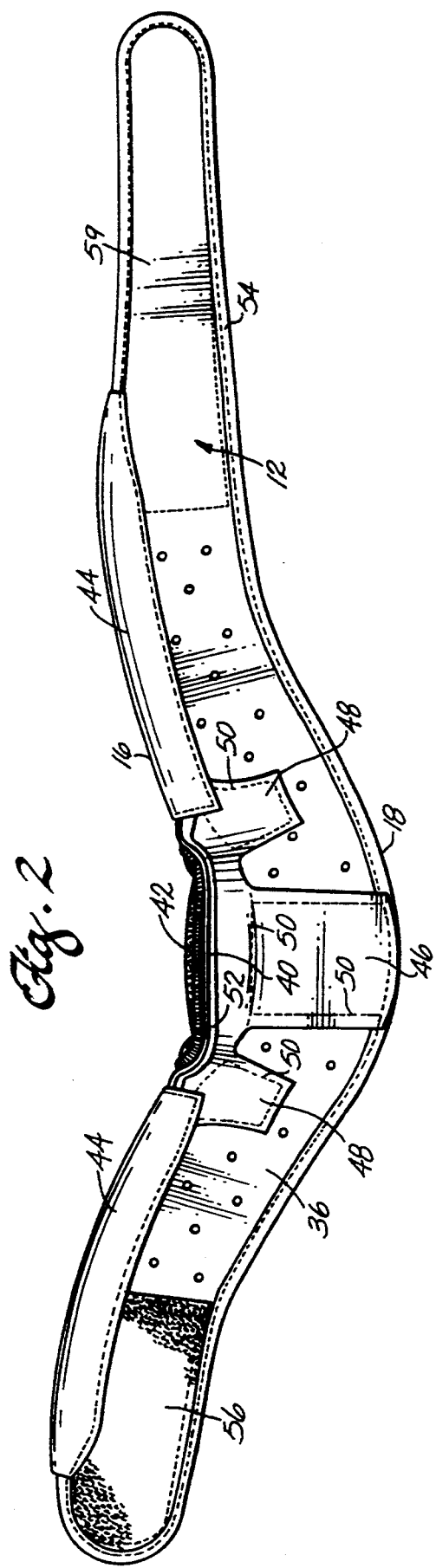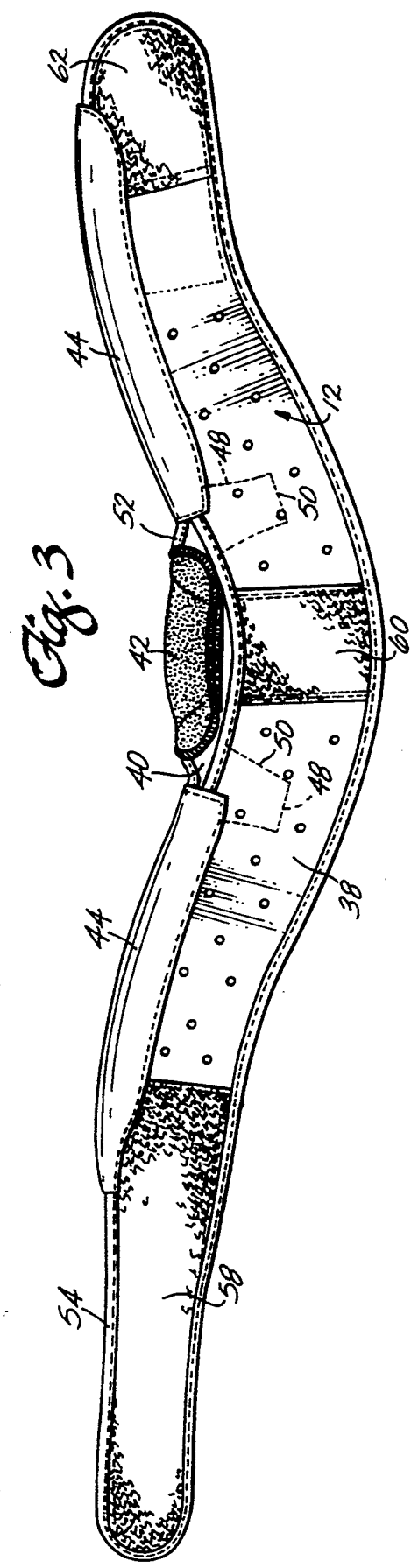

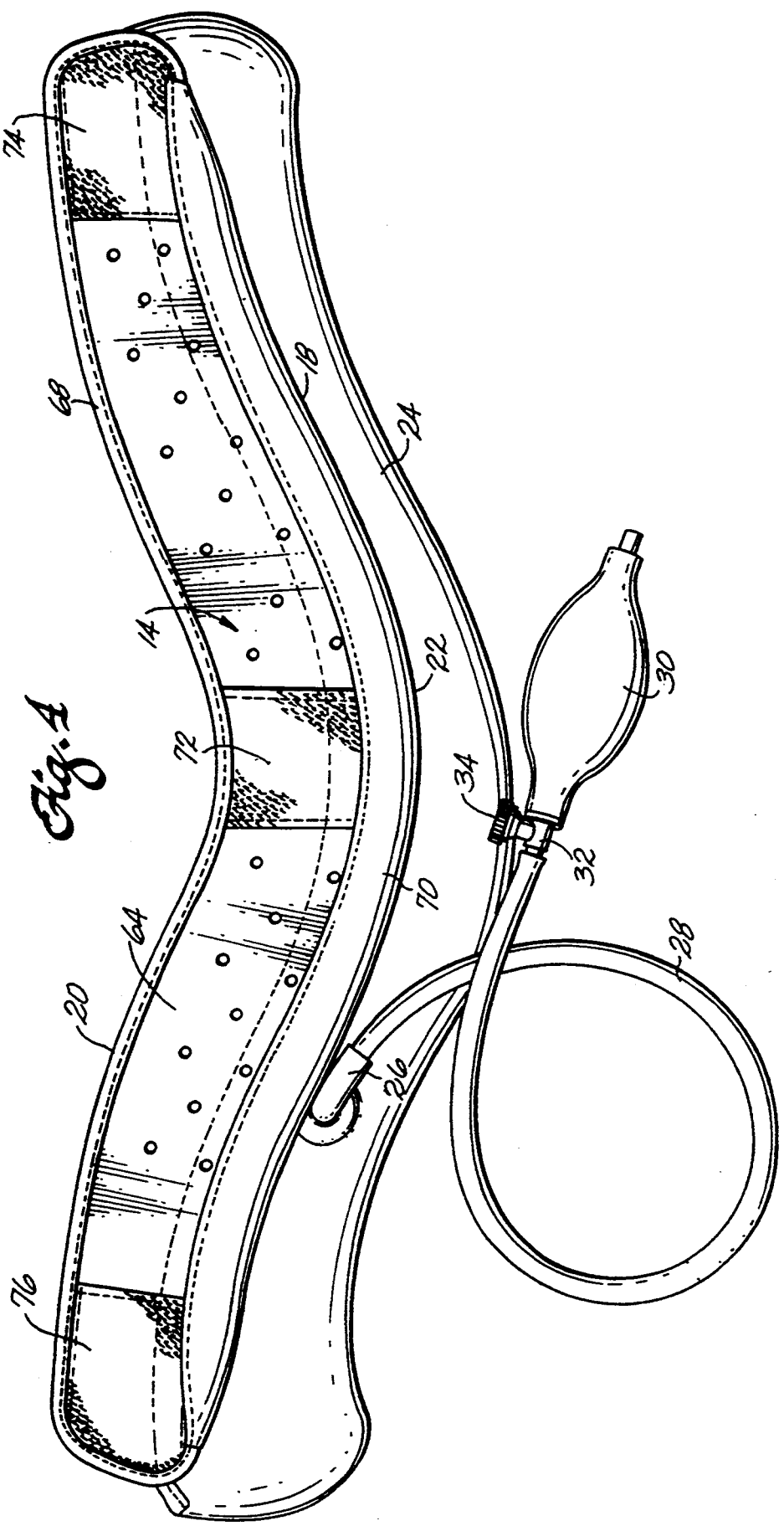

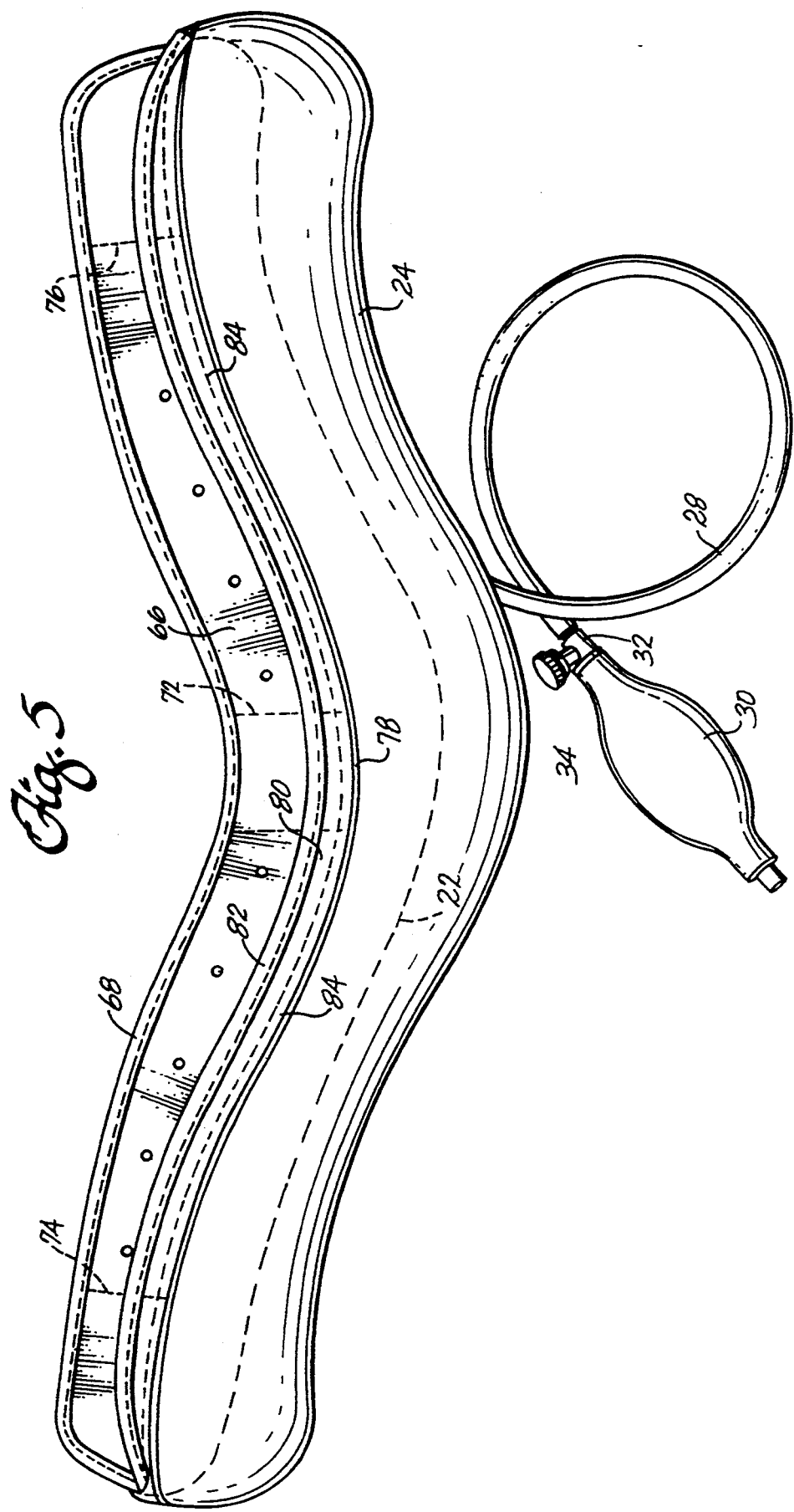

INFLATABLE CERVICAL TRACTION COLLAR

FIELD OF THE INVENTION

This invention relates to cervical traction devices, and more particularly, to a cervical collar which applies a carefully controlled amount of static traction around the neck while allowing ambulatory use by the patient.

BACKGROUND OF THE INVENTION

Treatment of cervical injuries or disorders often requires cervical traction for treating trauma to the muscles and ligaments of the neck and the cervical and upper thoracic vertebrae and associated spinal nerves. By applying cervical traction, a "cervical separation" is produced which alleviates pain caused by compression on the nerves, while allowing more blood flow to the affected tissue that speeds the healing process.

Normally, in the early stages of applying traction, cervical traction forces are most easily controlled when the patient is confined to a hospital bed where complex and expensive traction equipment is carefully controlled by medical professionals. When the patient has reached a point in the healing process where such clinical treatment is not needed, other controlled traction devices may be prescribed and used by the patient.

One such home use traction device is an "overdoor" cervical traction system in which traction forces are applied to a head halter or harness placed under the chin and occipital lobe areas. The harness is connected to a hanger that attaches to a door and holds a water filled weight bag that applies a controlled amount of upward traction force on the harness by gravity while the patient sits next to the door that supports the hanger and weight bag. This traction system applies traction forces by the weight bag pulling the harness upwardly from below the chin region and the base of the skull. The amount of water contained in a weight bag controls the amount of traction force. Although this system is useful, it requires a patient to sit in one place for long periods of time.

Another prior art patient-controlled cervical traction device is available under the name Pronex from Glacier Cross, Inc. This device includes a U-shaped block that fits behind the patient's neck and rests on the patient's shoulders. An air-inflatable bellows in the middle of the block applies lateral lifting forces upwardly to pillows on opposite sides of the patient's neck. This device requires the patient to be in bed while traction is applied. The traction force is not uniform around the entire neck region, and the bellows, being located at the middle of the device, can apply undesired inward pressure to the middle of the patient's neck and windpipe.

The present invention provides a cervical traction collar that can be used by the patient to apply a carefully controlled amount of traction force to the cervical region constantly while the patient is completely ambulatory. The cervical traction collar of this invention also applies a more uniform traction force than that produced by the harness used in the overdoor traction system.

SUMMARY OF THE INVENTION

Briefly, the present invention provides a cervical traction collar which includes an elongated semi-rigid flexible support member for extending around the neck region of a patient. The support member has an upper edge with chin support means for positioning below the chin and upper neck support means extending away from the chin support for encircling the upper neck region of the patient. The support member also includes a lower edge for encircling a lower portion of the neck region. An elongated, tubular, flexible, air-impervious bladder is secured to the support member so as to extend continuously along the support member while also projecting downwardly away from and spaced below the lower edge of the support member continuously around the circumference. The opposite ends of the support member are releasably secured together to hold the support member in a position encircling the neck region of the patient, with the upper edge thereof supporting the chin and upper neck region of patient, while the tubular bladder extends continuously around the upper shoulder region at the base of the patient's lower neck region. Means are provided for supplying fluid under pressure to the interior of the bladder for expanding the bladder downwardly in a direction away from the lower edge of the support member. This applies a continuous force encircling the support member and directed toward the shoulder region which in turn resists this downward force and applies a controlled amount of upward circumferential traction force uniformly to the cervical region of the patient.

The cervical traction collar of this invention provides a number of improvements for cervical traction therapy. The patient is completely ambulatory while the traction device is in use; the traction collar can be easily applied and quickly released; the patient can accurately control the pressure level of the traction force; the collar can be manufactured at a relatively low cost; the stabilizing effect of the applied traction force is continuous uniformly around the entire cervical region; and the collar can be made in a few select sizes to fit all sizes of patients.

These and other aspects of the invention will be more fully understood by referring to the following detailed description and the accompanying drawings.

BRIEF DESCRIPTION OF THE DRAWINGS

FIG. 2 is a front elevational view showing a front side of an upper support member of the collar.

FIG. 3 is a rear elevational view showing a rear side of the upper support member shown in FIG. 2.

FIG. 4 is a front elevational view showing a front side of a lower flexible collar and air inflatable bladder.

FIG. 5 is a rear elevational view showing a rear side of the lower support member shown in FIG. 4.

DETAILED DESCRIPTION

Figure 1:
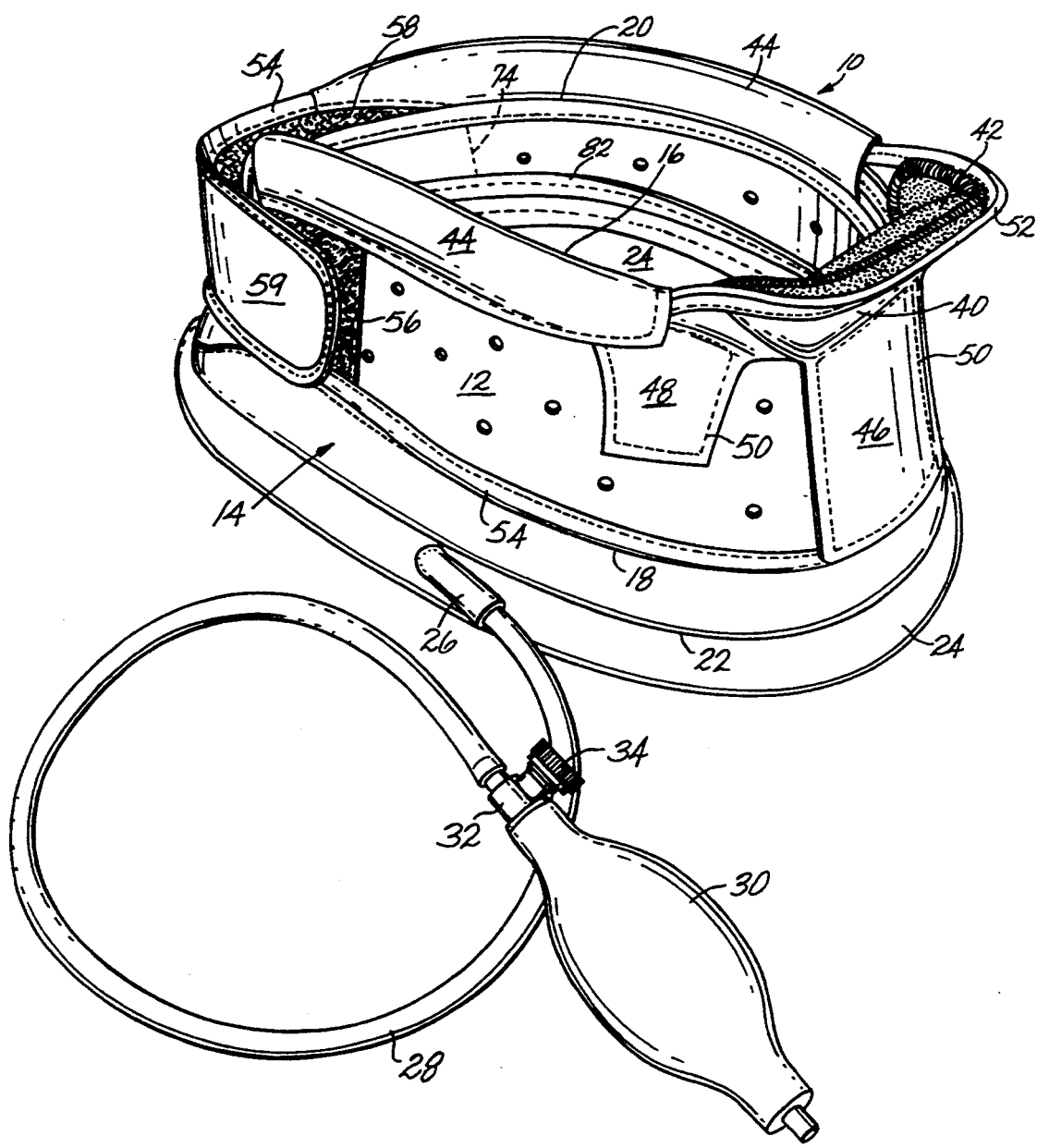
FIG. 1 is a perspective view showing an inflatable cervical traction collar according to principles of this invention.

FIG. 1 is a perspective view illustrating an inflatable cervical traction collar 10 according to principles of this invention. The traction collar is a two piece unit which includes an elongated semi-rigid flexible upper support member 12 having longitudinally extending upper and lower edges 14 and 16, respectively, and an elongated semi-rigid flexible lower support member 18 having longitudinally extending upper and lower edges 20 and 22, respectively. The upper and lower support members are each generally long, narrow and sinusoidal in shape so that when overlaid and secured to one another in a generally parallel relationship they provide support and conform to the chin, left and right mandibular and occipital regions, the shoulders, and the upper chest and back regions of a patient wearing the collar. Each support member is made from a durable flexible light weight plastic material such as polyethylene. In a preferred embodiment, the upper support member is adapted to overly the front face of the lower support member, and the two support members are releasably secured by cooperating Velcro fasteners as described below; however, in an alternative embodiment, the lower support member can overly and be releasably secured to the upper support member. The purpose of the two support members is to adjust the amount of overlap between them so as to adjust the effective height of the collar as it fits around the patient's neck.

An elongated, flexible, tubular, air-impervious bladder is secured to the inside of the lower support member. The tubular bladder extends longitudinally and generally parallel to the length of the upper and lower support members. The bladder has a sufficient height so as to project downwardly away from the lower edge 22 of the lower support member continuously along the length of the lower support member. FIG. 1 shows the bladder in an inflated condition encircling the lower portion of the collar and projecting downwardly from the bottom of the collar by a generally uniform distance around the entire base of the collar.

FIG. 1 also shows an arrangement for inflating the bladder 24 which includes a sleeve 26 rigidly secured to an opening to the interior of the bladder, and an elongated flexible tube 28 extending from the sleeve to a hand-actuated air pump 30 at the free end of the tube 28. An air valve 32 in the line between the air pump and the tube has a screw-threaded valve stem 34 that can be opened to allow inflation and then closed to retain the inflated air pressure in the bladder.

FIGS. 2 and 3 illustrate detailed construction of the upper support member which includes an outer face 36 (FIG. 2) and an inner face (FIG. 3). A generally U-shaped chin support 40 projects upwardly and outwardly from the front face of the upper support member. The inside surface of the chin support includes resilient padding 42. A pair of elongated left and right cushion pads 44 on the upper edges of the support member extend away from opposite sides of the chin support. The chin support is an integral part of a flexible plastic piece that overlies the front face of the support member. The flexible piece includes a central section 46 below the chin support and a pair of tabs 48 overlying the support member on opposite sides of the chin support. The central section and tabs are secured to the support member by corresponding rows of stitching 50. A soft flexible reinforcing edge 52 is stitched to and extends along the top of the chin support between the left and right cushioned pads 44. The remaining upper and lower edge portions of the upper support member are reinforced by a soft reinforcing pad 54. An elongated friction fastener section 56 preferably made of a Velcro hook material extends along one end of the outer face 36 of the upper support member for about one-half the distance from the end of the support member to the chin support. The function fastener section 56 is about four inches in length. On the opposite inside face 38 of the support member an elongated friction fastener section 58, preferably made from a Velcro pile material extends along the opposite end of the support member for about one-half the distance from the end of the support member to the chin support. The function fastener section 58 is about nine inches in length and covers the inside face of a long flexible fastener section 59 of the upper support member. By overlaying and securing the friction fastener sections 58 and 56, the upper support member can be releasably fastened in a loop of infinitely adjustable length as shown best in FIG. 1.

The inside face of the upper support member also includes a friction fastener section 60 preferably made from a Velcro pile material and extending centrally along the inside surface of the support member below the chin strap. An elongated friction fastener section 62 also preferably made from a Velcro pile material extends for a short distance away from the end of the upper support member opposite from the long friction fastener section 58. The friction fastener sections 60 and 62, together with a portion of the long friction fastener section 58, all of which are preferably made from the Velcro pile material, are used for releasably attaching the upper support member over the outer face of the inner support member in the manner described below.

FIGS. 4 and 5 illustrate detailed construction of the lower support member 14 which includes an outer face 64 (FIG. 4) and an inner face 66 (FIG. 5). The upper edge 20 of the lower support member is reinforced by a length of soft reinforcing material 68 stitched to and extending continuously for the length of lower support member. The reinforcing material 68 extends around the outer ends of the lower support member, with the remaining lower edge of the support member being padded continuously along its length by an elongated cushion pad 70. The cushion pads 44 and 70 are preferably made from a tubular core of a soft flexible fibrous material, or a resilient material such as cross-linked polyethylene foam, enclosed in an outer covering of a soft pliable material such as vinyl.

The outer face of the lower support member also includes three short sections of friction fastener material which include a central fastener section 72 and outer sections 74 and 76, each of which is made preferably from a Velcro hook material.

Referring to FIG. 5, the inside face 66 of the lower support member includes means for rigidly securing the air inflatable bladder 24 to the lower support member. The air inflatable bladder is preferably an elongated sinusoidal shaped tubular air-impervious bladder made from a flexible plastic material such as vinyl or polyethylene which can expand with fluid under pressure admitted to the hollow interior of the tube. In one embodiment, the bladder is made from 12 mil thick flexible inflatable vinyl. The bladder is preferably made by overlapping opposite faces of the plastic film and heat sealing edge portions of the film to form a tubular air inflatable member. This includes an elongated heat seal 78 formed along an upper edge of the tubular air inflatable bladder. The material from which the bladder is made also includes a narrow single ply section 80 projecting upwardly away from the sealed bladder and overlying the inside face of the lower support member to form a long flexible flap. A reinforced edge 82 formed by a soft reinforcing material is stitched to the long upper edge of the flap 80. A row of stitching 84 rigidly secures this flexible flap of plastic material to the inside face of the lower support member so that the bladder 24 projects freely downwardly away from the lower edge 22 of the lower support member 14 as shown best in FIG. 5. The bladder projects below the lower edge continuously along the entire length of the lower support member, and in one embodiment, the height of the projecting lower portion of the bladder is about one to 1½ inches below the lower edge 22.

Figure 6:
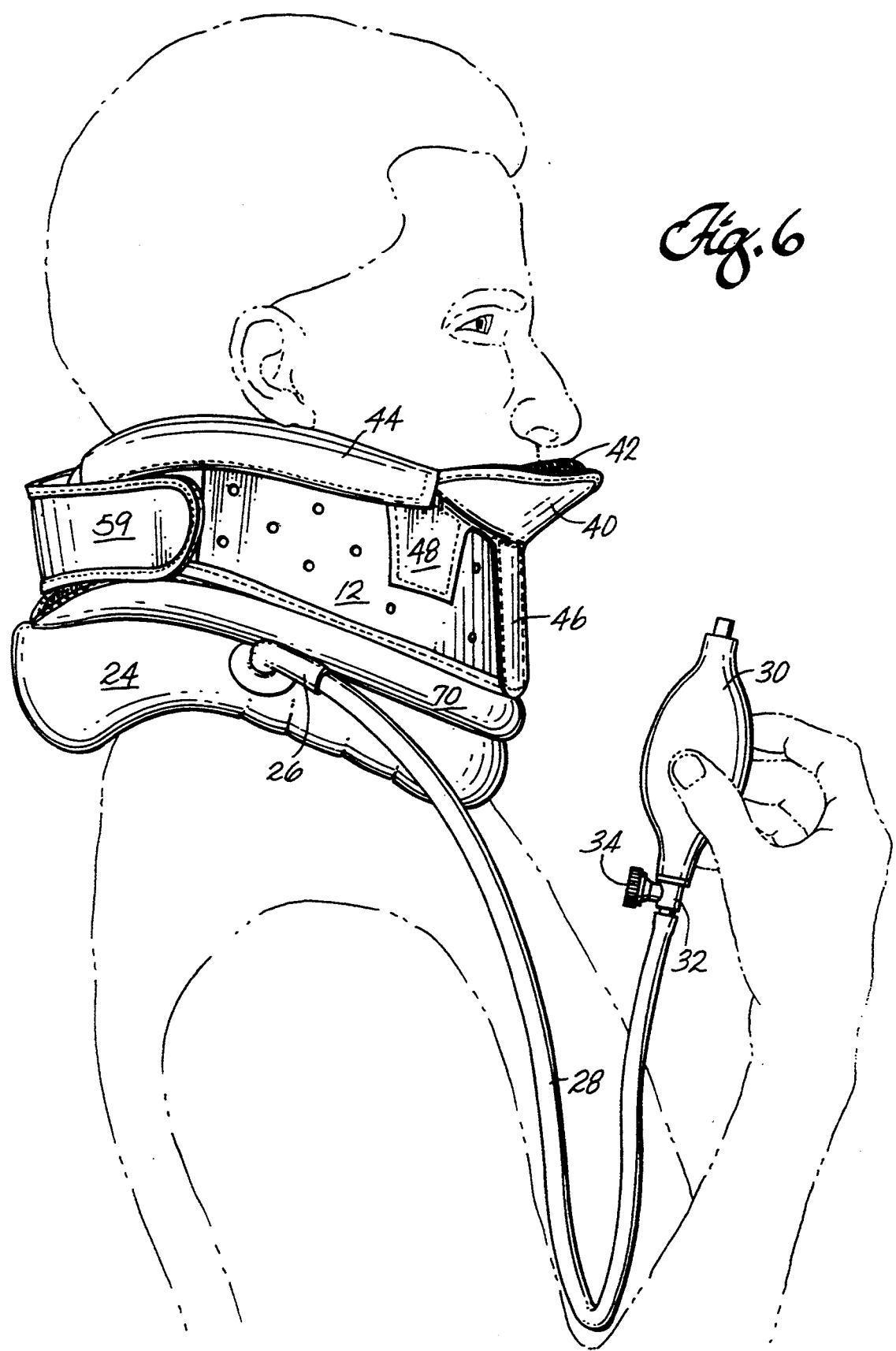
FIG. 6 is a side elevational view showing the inflatable cervical traction collar in an inflated traction producing position.

In using the traction collar, the upper support member 12 overlaps the lower support member 14 so that the cooperating friction fasteners 72, 74 and 76 on the front face of the lower support member are secured to the friction fasteners 58, 60 and 62 on the inside face of the upper support member. The height of the collar can be adjusted to the neck size of the patient by adjusting the amount of overlap in the regions of contact between the cooperating friction fasteners. The free end portion of the friction fastener 58 at the end 59 of the upper support member is then frictionally secured to the friction fastener 56 at the opposite end of the upper support member to hold the collar in a position encircling the neck region of the patient at the adjusted height. FIG. 6 best illustrates the cervical collar in a position encircling the neck region of the patient following the proper height adjustment.

Figure 7:
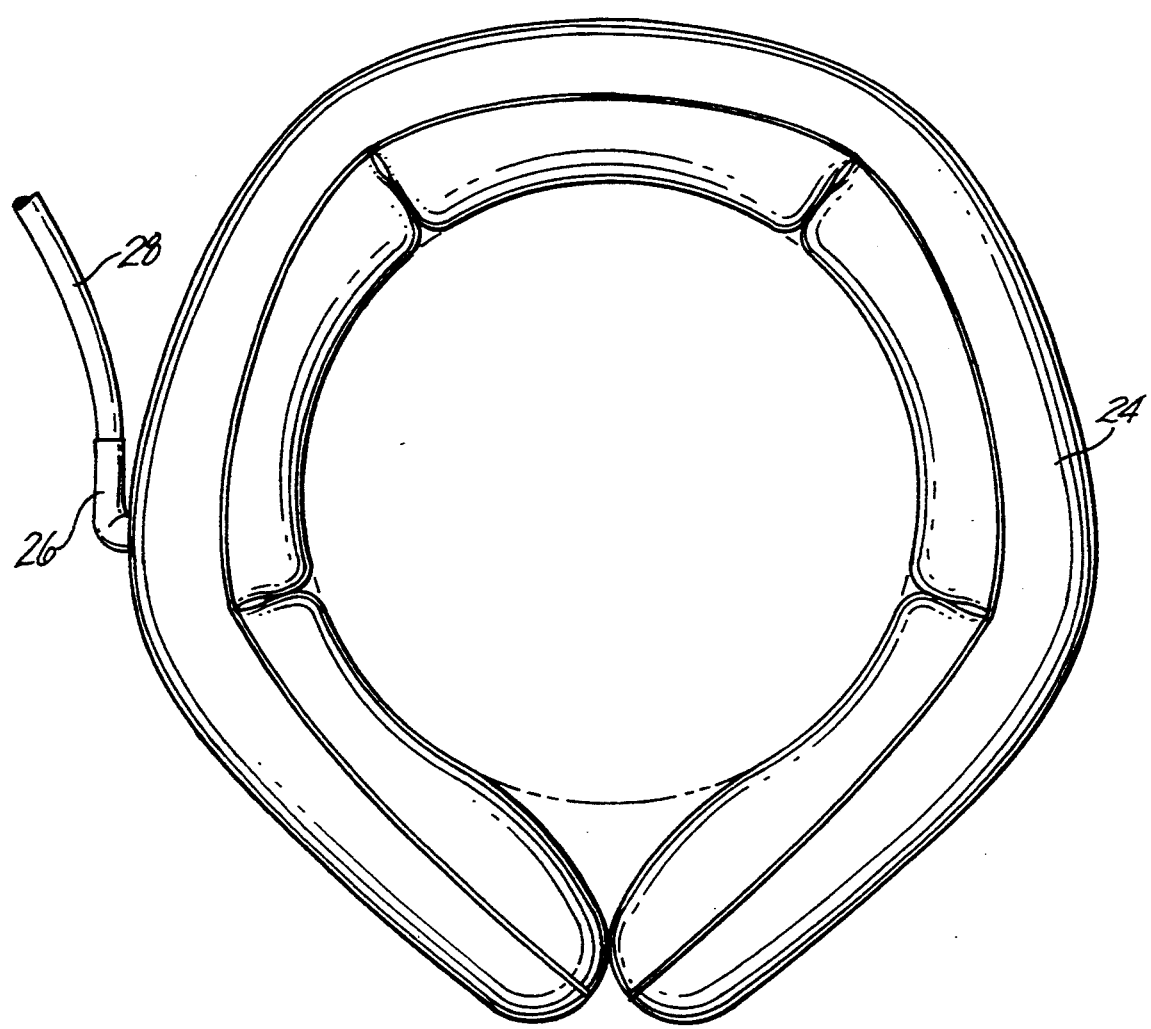
FIG. 7 is a bottom elevational view showing the inflated bladder encircling a lower circumferential portion of the collar.

The bladder 24 projects downwardly below the lower edge 22 of the lower support member 14 continuously around the entire outer circumference of the cervical collar. With the patient's chin on the chin support and the upper edge of the collar supporting the left and right mandibular and occipital regions of the patient's neck, the cervical traction device is then ready for air inflation for applying a traction force to the cervical region of the patient. As shown best in FIG. 6, the air pump is manually pressurized for forcing air under pressure into the hollow interior of the tubular air-inflated bladder 24. The bladder expands under increasing pressure build up and presses downwardly against the shoulders of the patient continuously in a complete circle around the lower neck region of the patient. As shown best in FIG. 7, the air inflated bladder completely encircles the base of the collar. The force of the inflated bladder is resisted by the shoulders and upper chest and back regions, which produces a generally uniform circumferentially directed upward force on the upper neck region of the patient continuously around the chin, the left and right mandibular, and left and right occipital regions of the patient, which applies a generally uniform traction force to the cervical region of the patient.

Once the proper inflating pressure and resulting traction force is produced, the air valve can be tightened to retain the pressure and therefore the traction force. To enhance mobility of the patient, the air supply tube can have disconnect fitting at the air bladder to separate the air pump and hose from the rest of the cervical collar.

Good traction force is applied when the bladder 24 is inflated to an air pressure above about 3.5 to about 4 psi. The air valve 32 can include a pressure-sensitive air relief valve for bleeding off air to the atmosphere if sensed air pressure in the bladder exceeds a maximum preset level.

The long lengths of overlapping Velcro friction fasteners assist in resisting the rear strap 59 from pulling away or twisting off under forces generated when the bladder is inflated.

The particular type of Velcro material also found useful for this purpose is available from Velcro Co. under HTH 705 hook and 1000 loop.

What is claimed is:

1. A cervical traction collar comprising:

an elongated flexible support member for extending around the neck region of a patient, the support member comprising longitudinally extending upper and lower sections independently adjustable relative to each other with fastener means for releasably securing the upper and lower sections together as a unit to form a collar of adjustable height continuously around the neck region of the patent, the upper section of the support member having an upper edge with (a) chin support means for positioning below the chin, and (b) upper neck support means for encircling the upper neck region of the patient, the lower section of the support member having a lower edge for encircling a lower neck region of the patient, the upper and lower sections of said support member each comprising a long, narrow strap made from a soft, flexible plastic material for easily conforming to the anatomical shape of the neck region of the patient as the upper and lower sections are positioned relative to one another, adjusted in relative position to each other, and adhered to one another by said fastener means;

means for releasably securing opposite ends of the support member to hold the support member in said adjusted position encircling the neck region of the patient;

an elongated, tubular, flexible, air-impervious bladder secured to the support member so as to extend continuously along the support member while projecting downwardly away from and spaced below the lower edge of the support member continuously along the length of the support member when the support member is secured in its position for encircling the neck region of the patient;

the upper edge of the support member supporting the chin and upper neck region of the patient while the tubular bladder freely extends continuously around the upper shoulder region at the base of the patient's lower neck region spaced below the lower edge of the support member; and means for supplying fluid under pressure to the interior of the bladder for expanding the bladder downwardly in a direction below the lower edge of the support member toward the shoulder region of the patient which produces a resistance force acting upwardly to apply a controlled amount of upward traction force uniformly around the upper neck region of the patient.

2. Apparatus according to claim 1 in which the air-inflatable bladder is supported freely from a flexible flap extending longitudinally and secured to the support member.

3. Apparatus according to claim 2, in which the air-inflatable bladder is supported freely from a flexible flap which comprises a sheet of plastic film integral with the wall of the bladder.

4. Apparatus according to claim 1 in which the means for supplying fluid under pressure includes a pressure sensitive air relief valve to limit air pressure within the bladder to a preset level.

5. Apparatus according to claim 1 in which the means for supplying fluid under pressure includes a pressure sensitive air relief valve to limit air pressure within the bladder to a preset level.

6. Apparatus according to claim 1 in which the preset air pressure level is at least about 3.5 psi.

7. Apparatus according to claim 1 in which the upper and lower sections of the support member are separate and independent from one another and each includes friction fastener means for releasably securing the upper and lower sections together as a unit.

* * * * *